(12) United States Patent  
Takala et al.

(10) Patent No.: US 7,549,959 B2  
(45) Date of Patent: Jun. 23, 2009

(54) STIMULATION ARRANGEMENT FOR MEASUREMENT OF PHYSIOLOGICAL SIGNAL REACTIVITY

(75) Inventors: Panu Takala, Helsinki (FI); Juha Virtanen, Helsinki (FI)

(73) Assignee: The General Electric Company, Schenectady, NY (US)

( * ) Notice: Subject to any disclaimer, the term of this patent is extended or adjusted under 35 U.S.C. 154(b) by 20 days.

(21) Appl. No.: 11/743,834

(22) Filed: May 3, 2007

(65) Prior Publication Data

US 2008/0275347 A1    Nov. 6, 2008

(51) Int. Cl.  
*A61B 5/00* (2006.01)  
*A61B 5/02* (2006.01)

(52) U.S. Cl. .............. 600/300; 600/508; 600/544; 600/545

(58) Field of Classification Search .......... 600/378, 600/544, 481, 393, 300, 559, 554, 546; 607/45; 604/503

See application file for complete search history.

(56) References Cited

U.S. PATENT DOCUMENTS

| | | | | |
|---|---|---|---|---|
| 4,201,224 | A * | 5/1980 | John | 600/544 |
| 5,611,350 | A * | 3/1997 | John | 600/378 |
| 6,083,156 | A * | 7/2000 | Lisiecki | 600/301 |
| 7,239,919 | B2 * | 7/2007 | Naisberg et al. | 607/45 |
| 2004/0147969 | A1 * | 7/2004 | Mann et al. | 607/17 |
| 2005/0085741 | A1 | 4/2005 | Hoskonen | |
| 2005/0165323 | A1 | 7/2005 | Montgomery et al. | |
| 2006/0167368 | A1 * | 7/2006 | Sarkela | 600/544 |
| 2006/0173510 | A1 | 8/2006 | Besio et al. | |
| 2006/0184059 | A1 | 8/2006 | Jadidi | |
| 2006/0241562 | A1 * | 10/2006 | John et al. | 604/503 |
| 2007/0015985 | A1 * | 1/2007 | Tolvanen-Laakso et al. | 600/393 |
| 2007/0067004 | A1 | 3/2007 | Boveja et al. | |
| 2007/0112278 | A1 * | 5/2007 | Viertio-Oja et al. | 600/559 |

OTHER PUBLICATIONS

"Measurement of EEG Reactivity", pending U.S. Appl. No. 11/273,574, filed Nov. 14, 2005, Viertio-Oja et al.  
"Measurement of EEG Reactivity", pending U.S. Appl. No. 11/674,732, filed Feb. 14, 2007, Sarkela et al.  
"An Electroencephalographic Classification for Coma" Young et al., Can. J. Neurol. Sco. 1997; 24:320-325.  
EP Search Report dated Sep. 11, 2008.  
Netherlands Novelty Search Report dated Oct. 28, 2008.

* cited by examiner

*Primary Examiner*—Robert L. Nasser, Jr.  
(74) *Attorney, Agent, or Firm*—Andrus, Sceales, Starke & Sawall, LLP

(57) ABSTRACT

The invention relates to a method and apparatus for assessing the reactivity observable in a certain physiological signal, especially the EEG signal, of a subject. In order to obtain a compact measurement arrangement that enables reliable assessment of changes in the reactivity of the subject even during a long time period, a conventional monitoring device is provided with a stimulation module configured to supply stimuli to the subject through a measurement probe that the device uses to receive physiological signal data from the subject. The measurement probe may comprise, for example, an arm cuff through which the device monitors the blood pressure of the subject.

20 Claims, 4 Drawing Sheets

STIMULATION ARRANGEMENT FOR MEASUREMENT OF PHYSIOLOGICAL SIGNAL REACTIVITY

FIELD OF THE INVENTION

The present invention relates to the assessment of the reactivity of the central nervous system of a patient by applying an external stimulation to the patient. The stimulation is observable on/in a physiological signal, especially an EEG signal. Below, the reactivity observable on/in a physiological signal is termed physiological signal reactivity.

BACKGROUND OF THE INVENTION

Neuromonitoring is a subfield of clinical patient monitoring focused on measuring various aspects of brain function and on changes therein caused by neurological diseases, accidents, and drugs commonly used to induce and maintain anesthesia in an operation room or sedation in patients under critical or intensive care.

Electroencephalography (EEG) is a well-established method for assessing brain activity. When measurement electrodes are attached on the skin of the skull surface, the weak biopotential signals generated in brain cortex may be recorded and analyzed. The EEG has been in wide use for decades in basic research of the neural systems of the brain as well as in the clinical diagnosis of various central nervous system diseases and disorders.

While spontaneous variation in a wake-sleep cycle causes physiological and rapidly reversible changes in the EEG, different derangements of internal system homeostasis disturb the environment in which the brain operates, and therefore the function of the brain and the resulting EEG are disturbed. The EEG signal is a very sensitive measure of the neuronal derangements, which may reflect in the EEG signal either as changes in membrane potentials or as changes in synaptic transmission. A change in synaptic transmission occurs whenever there is an imbalance between consumption and supply of energy in the brain. This means that the EEG signal serves as an early warning of a developing injury in the brain.

Generally, if a patient is unconscious (without sedation), the reason in 30 to 40 percent of the cases is intracranial, whereas in 60 to 70 percent of the cases unconsciousness is due to hypoxic-ischaemic, metabolic, or toxic reasons. This kind of general unconsciousness is currently monitored with the help of the Glasgow Coma Scale (GCS). It defines the patient (un)consciousness by using three parameters: the best eye opening response, the best motoric response, and best response to speech. The final score represents the sum of the scores of the three categories. Although the Glasgow Coma Scale is subjective and inter-rater variability may exist, it is the most widely used scoring system to assess patients with traumatic brain injury, for example.

Diagnostically, the EEG is only rarely specific, since many systemic disorders of the brain produce similar EEG manifestations. However, an EEG signal may be of critical value, as it may differentiate between broad categories of psychogenic, epileptic, metabolic-toxic, encephalitic, and focal conditions, for example.

In a healthy sleeping subject, the EEG is reactive to various stimuli depending on the sleep stages. For a comatose patient, a test of the reactivity of the EEG signal to external stimulation is an important assessment tool for a clinician, since it provides significant information regarding the state and outcome of the patient. EEG reactivity may reveal potentially treatable conditions and also provide information of the level of drug-induced sedation. While some conclusions about the probability of a recovery can be drawn from the raw EEG signal as such, it has been shown that reactivity of the EEG signal to stimulation, i.e. a detectable change in the EEG signal after a stimulus as compared to the pre-stimulus situation, is a more specific indicator of a favorable outcome, cf. G. B. Young, et al: An Electroencephalographic Classification for Coma, Can. J. Neurol. Sci. 1997; 24: 320-325. Therefore, testing the EEG reactivity is an essential part of the EEG examination of a comatose patient. Moreover, the test of EEG reactivity provides information regarding the state of a patient for whom the GCS or another observational scoring system is not applicable. This is the case, for example, when neuromuscular blocking agents have been administered to the patient, which makes the patient unable to respond and thus the observational scoring systems inapplicable.

At present, the EEG reactivity is assessed by an EEG specialist trained to interpret EEG waveforms. In practice, ICU (Intense Care Unit) doctors or nurses, who are skilled in making GCS-type assessments, are usually not capable of interpreting the EEG waveforms, and therefore a consulting EEG specialist has to be called in for the test of EEG reactivity. Various types of stimuli, such as auditory (shouting the patient's name, blowing a horn) and somatosensory (pinching, squeezing, shaking) stimuli, may be applied in the test. The EEG specialist annotates the time instant of the stimulation and compares the recorded EEG signal before and after the annotated time instant. Often the EEG signal shows reactivity only to some of the given stimuli; in this case reactivity is considered to be present.

The test of the EEG reactivity is currently based mainly on manual stimulation performed by a nurse or a doctor, despite the fact that its intensity is often subject to variability between stimulators. The stimulation is typically given by manually touching the patient, i.e. the stimulation is sensed by the somatosensory system of the patient. Even if the same person repeats stimulation, its intensity may vary. Comparison of EEG reactivity between different stimulations is in this case difficult because a more intense stimulus may result in a higher response in the EEG signal than a milder stimulus. Standardized stimulation intensity would enable the evaluation of changes in patient's reactivity over a longer time period.

Standardized stimulation intensity can be achieved with an automatic stimulation device, such as an NMT (NeuroMuscular Transmission) module, which is used for evaluating muscle response by stimulating a peripheral nerve. However, the use of an automatic stimulation device capable of producing a standard stimulation pattern similar to the manual stimulation given by the nursing staff requires normally a dedicated actuator. This is a drawback especially in Intensive Care Units (ICU) and in operation rooms which tend to be crammed with medical appliances. Healthcare professionals are therefore reluctant to introduce new appliances to such points of care. This drawback may be alleviated to some degree by using a sensor arrangement in which all electrodes and sensors may be connected to a single connector, whereby the amount of cables or hoses between the patient and the monitoring devices may be reduced. A sensor arrangement like this is disclosed in U.S. Patent Application 2005/0085741 A1. The sensor arrangement comprises separate NMT electrodes to stimulate the facial nerves of the patient, and the NMT response is measured through recording electrodes or a mechanical sensor located in the facial area of the patient.

Another drawback related to manual stimulation is that the annotation of the time of the stimulation in the EEG signal may not always be accurate. A precise annotation of the stimulation instant in the EEG signal would facilitate more advanced signal analysis methods, for example averaging of responses to several stimuli.

Consequently, the test of EEG reactivity is complicated by the lack of a compact and automated stimulation arrangement that can provide constant stimulation patterns similar to or simulating the manual stimulation given by the nursing staff, and allows precise annotation of each stimulus with respect to the EEG waveform.

The present invention seeks to alleviate or eliminate the above-mentioned drawbacks.

SUMMARY OF THE INVENTION

The present invention seeks to provide a novel mechanism for estimating the physiological signal reactivity, especially EEG reactivity of a subject. The present invention further seeks to provide an automated measuring arrangement which is easy to introduce in points of care with limited or no space for additional equipment, which enables reliable assessment of changes in the physiological signal reactivity of the subject even during a long time period, and which may stimulate the patient naturally as a doctor or nurse.

In a standard patient monitoring device one or more physiological signals, such as an EEG signal, an ECG (electrocardiogram) signal and/or a non-invasive blood pressure (NIBP) signal, are measured from a patient through measurement probes specific to each physiological signal. In this context, a measurement probe refers to the sensor elements attached to the patient, while the patient monitoring device refers to the actual measurement device that indicates the measurement results to the user. The measurement probe thus refers to the elements supplying the measured biosignal to the patient monitoring device. The measurement probe may comprise a set of electrodes, such as EEG or ECG electrodes, or an arm cuff, such as a NIBP arm cuff.

In the present invention, a standard patient monitoring device is complemented with integrated stimulation functionality that utilizes the existing measurement probe(s) of the device for supplying the stimuli to the patient.

In some embodiments of the invention, the stimuli are supplied through the arm cuff of a NIBP probe, while in some other embodiments TENS (transcutaneous electrical nerve stimulation) type functionality, which is normally used for massaging muscles or providing pain relief, is combined with the measurement of physiological signal reactivity without adding to the hardware required.

The stimuli may be supplied to a NIBP probe when a NIBP measurement is not in progress or the inflation of the cuff during a blood pressure measurement may be utilized as a stimulus for the reactivity measurement. However, electrical stimuli similar to those produced by an NMT module may also be supplied through electrodes attached to the skin of the patient. The said electrodes may be, for example, the EEG or ECG electrodes of the patient monitoring device.

Thus one aspect of the invention is providing a method for measuring the physiological signal reactivity of a subject. The method includes receiving physiological signal data from a subject through at least one measurement probe attached to the subject and supplying a stimulus to the subject through a first measurement probe, wherein the first measurement probe is one of the at least one measurement probe. The method further includes determining whether reactivity caused by the stimulus is present in physiological signal data received through a second measurement probe, wherein the second measurement probe is one of the at least one measurement probe.

Another aspect of the invention is that of providing an apparatus for measuring the physiological signal reactivity of a subject. The apparatus includes a measurement module configured to receive physiological signal data from a subject and at least one measurement probe attachable to the subject, the at least one measurement probe being configured to produce the physiological signal data. The apparatus further includes a stimulation module configured to stimulate the subject through a first measurement probe, wherein the first measurement probe is one of the at least one measurement probe and a reactivity determination module configured to determine whether reactivity caused by the stimulus is present in physiological signal data received through a second measurement probe, wherein the second measurement probe is one of the at least one measurement probe.

The patient monitoring device may stimulate the patient at desired time instants by pressurizing the NIBP arm cuff or supplying stimulating current to EEG/ECG electrodes attached to the subject. The invention thus provides an automated stimulation mechanism for the measurement of physiological signal reactivity without any additional probes, or effort from the healthcare personnel. Furthermore, the invention enables generation of stimuli similar to the manual stimulation given by the nursing staff. Especially, the present invention allows stimuli, which the patient feels similarly as the typical grabbing/shaking by a doctor or a nurse.

A further aspect of the invention is that of providing a computer program product by means of which known patient monitoring devices may be upgraded and thus their applicability extended to include the assessment of physiological signal reactivity. The program product comprises a first program code portion configured to trigger a stimulus to a subject through a first measurement probe, which is attached to the subject and configured to supply physiological signal data to a monitoring device and a second program code portion configured to determine whether reactivity caused by the stimulus is present in physiological signal data received from the subject through a second measurement probe.

The strength of the stimulation may be personalized for each patient. By increasing the strength of the stimulation stepwise and recording the respective physiological reactivity, a suitable strength of stimulation that provides desired level of reactivity may be found for each patient.

If the measurement probe is not moved and the strength of the stimulation is kept constant, the development of the patient's status may be monitored by recording changes in the reactivity to the constant stimulus. This enables the evaluation of the effect of sedative drugs administered to the patient and the information obtained may be used for finding an optimal dose.

A feature of the EEG signal, for example good signal quality or a desired level of central nervous system activation, may trigger automated stimulation and reactivity determination. A change in another physiological signal, such as ECG, may also trigger the stimulus and the reactivity determination.

The reactivity of the central nervous system of the subject may also be determined with respect to another physiological signal than the EEG, such as ECG.

The invention thus enables the generation of a standardized, repeatable, and personalized stimulus to a subject for evaluating physiological signal reactivity without the presence of a healthcare professional. It thereby enhances patient monitoring in an ICU environment.

Other features and advantages of the invention will become apparent by reference to the following detailed description and accompanying drawings.

BRIEF DESCRIPTION OF THE DRAWINGS

In the following, the invention and its preferred embodiments are described more closely with reference to the examples shown in FIG. 1 to 6 in the appended drawings, wherein.

Figure 5:
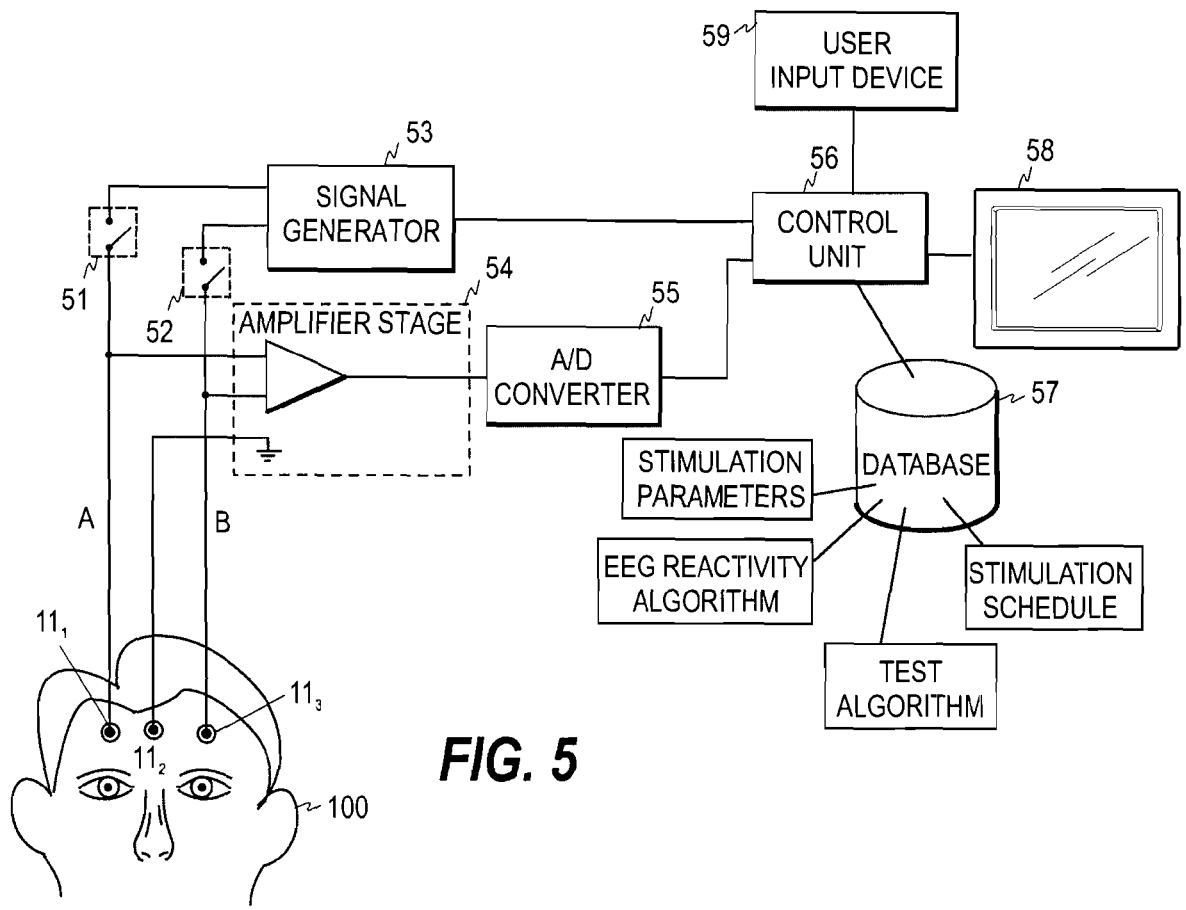
FIG. 5 illustrates one embodiment of the apparatus/system of the invention.

FIG: 6 illustrates an example of the functional entities of the control unit of FIG. 5.

DETAILED DESCRIPTION OF THE INVENTION

Figure 1:
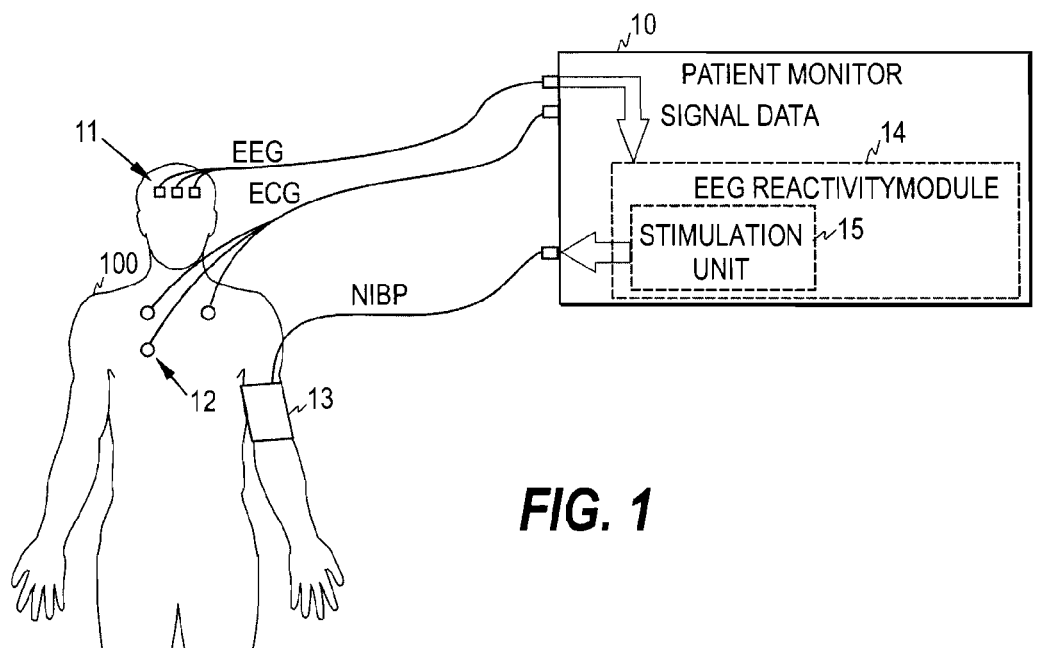
FIG. 1 illustrates one embodiment of the invention utilizing the NIBP measurement of a standard patient monitoring device.
Figure 2:
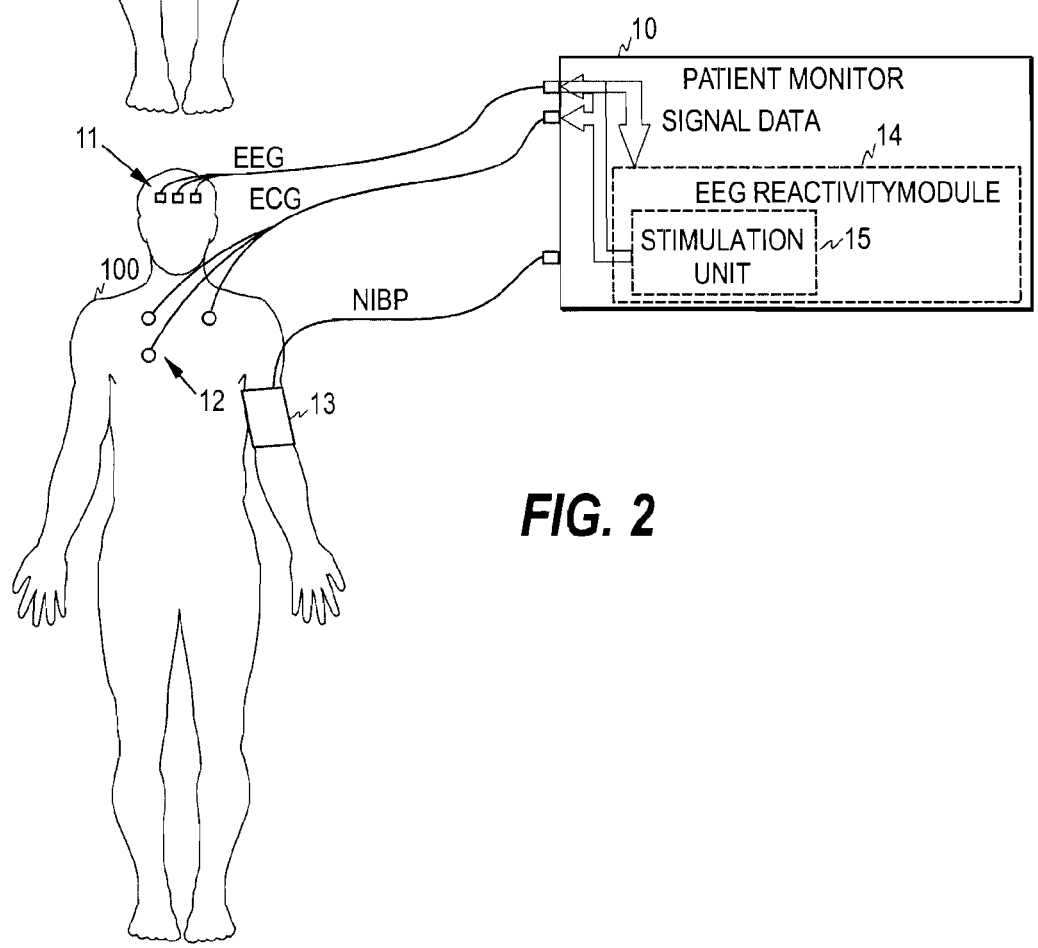
FIG. 2 illustrates other embodiments of the invention utilizing the EEG and/or ECG measurement of a standard patient monitoring device.

FIGS. 1 and 2 illustrate various embodiments of the invention for measuring EEG reactivity. As discussed above, in a standard patient monitoring device one or more physiological signals are measured from a patient through signal-specific measurement probes. FIGS. 1 and 2 show a patient monitoring device 10 capable of measuring EEG, ECG, and NIBP. The EEG is measured through a set of EEG electrodes 11 attached to the forehead of the patient 100, the ECG is measured through a set of ECG electrodes 12 attached to the chest of the patient, and NIBP is measured through an arm cuff 13 placed around the brachium of the patient. As is common in ECG and EEG measurements, the number and placement of the electrodes used may change depending on the measurement set-up.

The patient monitoring device 10 is provided with an EEG reactivity module 14 for measuring the EEG reactivity. For this purpose, the module receives EEG signal data measured through the EEG electrodes. The module further comprises a stimulation unit 15 for actively stimulating the patient for the evaluation of the reactivity.

In the embodiment of FIG. 1, the stimulation unit 15 is configured to control the inflation of the arm cuff 13. Since a conventional patient monitoring device is provided with a NIBP measurement, the EEG reactivity module may be introduced by providing the device with a software upgrade enabling the device to perform an EEG reactivity measurement in which the patient is stimulated by inflating the arm cuff to a predetermined pressure for a short period of time.

FIG. 2 illustrates other embodiments in which the stimulation is given by supplying electrical stimuli through selected EEG or ECG electrodes to the patient. In these embodiments, the EEG reactivity module is provided with a signal generator producing the electrical stimuli supplied to the said electrodes. The selected EEG or ECG electrodes typically comprise a subset of the EEG or ECG electrode set used by the device to measure EEG or ECG signal data.

The stimulation may also involve a combination of the above-mentioned stimuli.

Figure 3:
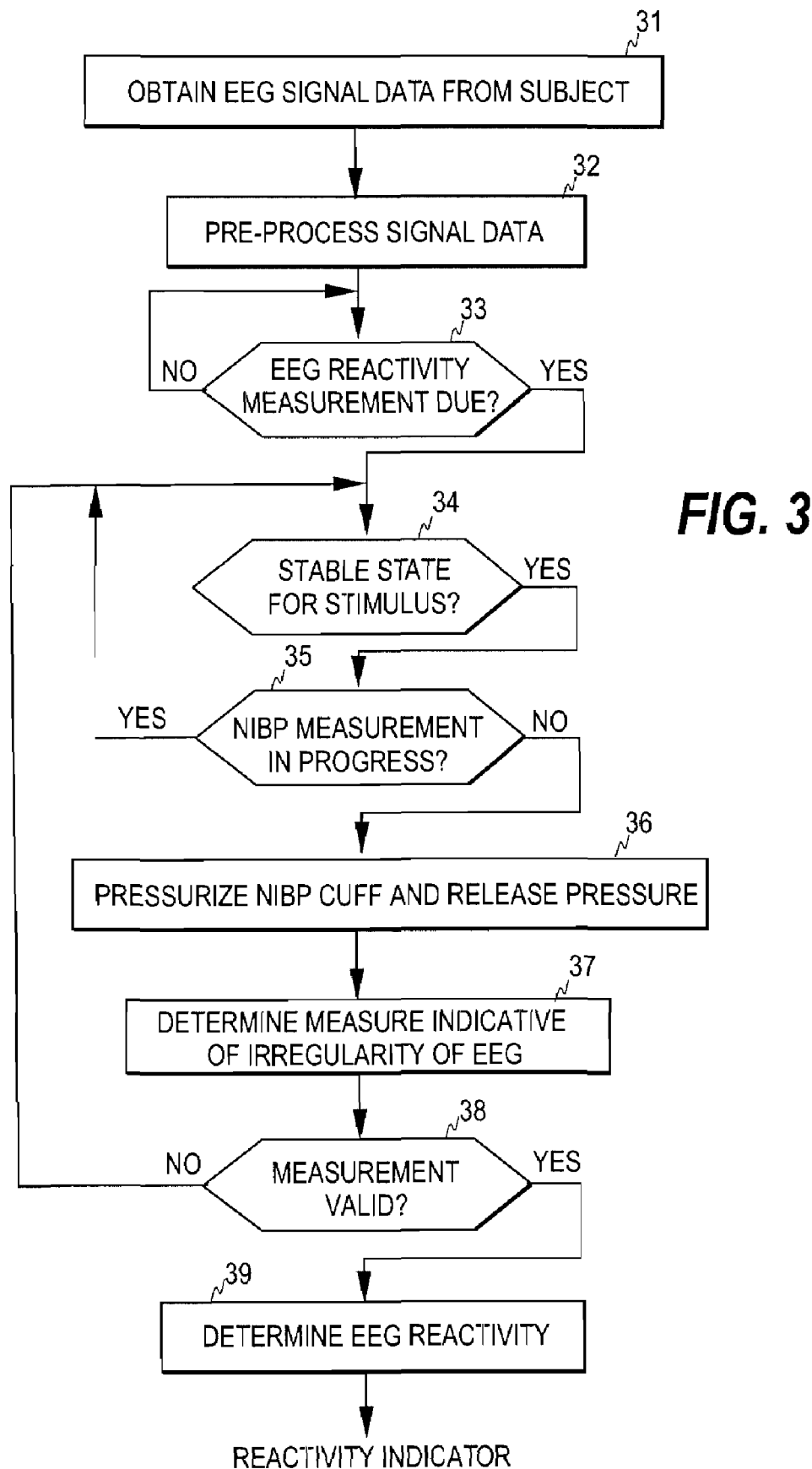
FIG. 3 is a flow diagram illustrating one embodiment for the reactivity determination in the embodiment of FIG. 1.

FIG. 3 illustrates one embodiment of the operation of the EEG reactivity module of FIG. 1. The EEG signal measured from the patient (step 31) is first digitized and the sampled EEG signal is filtered to exclude high- and low-frequency artifacts (step 32). As is common in the art, the digitized signal samples are processed as sets of sequential signal samples representing finite time blocks or time windows, commonly termed "epochs". When the reactivity measurement is due, the stimulus may be given if a stable state is detected for the stimulus and if a NIBP measurement is not in progress (steps 33-36). In this embodiment, the EEG reactivity module monitors the incoming EEG signal data to ensure that the EEG signal is stable enough prior to the application of the stimulus, i.e. that the signal does not include unwanted distortions when the stimulus is given. Furthermore, the EEG reactivity module monitors whether a NIBP measurement is in progress simultaneously in order not to stimulate the patient during the NIBP measurement.

If there is no simultaneous NIBP measurement and the EEG signal is stable enough, a stimulus is given (step 36) by pressurizing the arm cuff 13 and releasing the pressure according to a predetermined stimulation pattern, which defines the characteristics of the stimulation, such as the strength and duration of each stimulation pulse. The pattern may include one or more stimulation pulses. A time label indicating the time instant of the stimulus/stimuli is/are attached to the EEG signal data, i.e. the EEG signal data is temporally aligned with the time instant(s) of the stimulus/stimuli.

The response caused by the stimulus in the EEG signal is then detected by calculating a measure indicative of the irregularity of the EEG signal in successive time windows both prior to and after the stimulus signal (step 37).

Automatic EEG reactivity measurement based on a measure indicative of the irregularity of EEG is disclosed in Applicant's U.S. patent application Ser. No. 11/273,574. As discussed therein, the measure is typically spectral entropy, but several other types of entropies may also be utilized, such as Shannon entropy or approximate entropy. Such a measurement rests on the discovery that although various types of responses may appear in the EEG signal after a stimulus, the said responses are nevertheless such that they cause a change in the entropy of the EEG signal, or, more generally, in a measure indicative of the irregularity of the EEG signal. Therefore, the reactivity of the EEG may be quantified by measuring the change that stimulation causes in said measure.

Based on the successive irregularity values obtained from step 37, the process may then check whether the measurement is regarded as valid, i.e. whether the moment of the application of the stimulus was really a suitable moment for the measurement (step 38). If this is the case, the process calculates a measure indicative of the EEG reactivity of the subject (step 39). In the opposite case, the process returns to step 34 to detect a suitable moment to repeat the stimulation.

In the embodiment of FIG. 3, the reactivity measurement and the NIBP measurement are carried out as two separate measurements. However, they may also be combined so that the presence/absence or magnitude of reactivity is determined when the blood pressure is measured. For example, if the blood pressure of the patient is determined automatically at regular intervals, the apparatus may determine the presence/absence or magnitude of reactivity resulting from the inflation of the NIBP measurement cuff. In addition to such periodic measurements, the reactivity may also be determined whenever an event is detected that requires such a measurement. For example, if the EEG measurement indicates a change in the level of the consciousness of the patient or if a significant change is detected in the ECG, the EEG reactivity measurement may be triggered.

Figure 4:
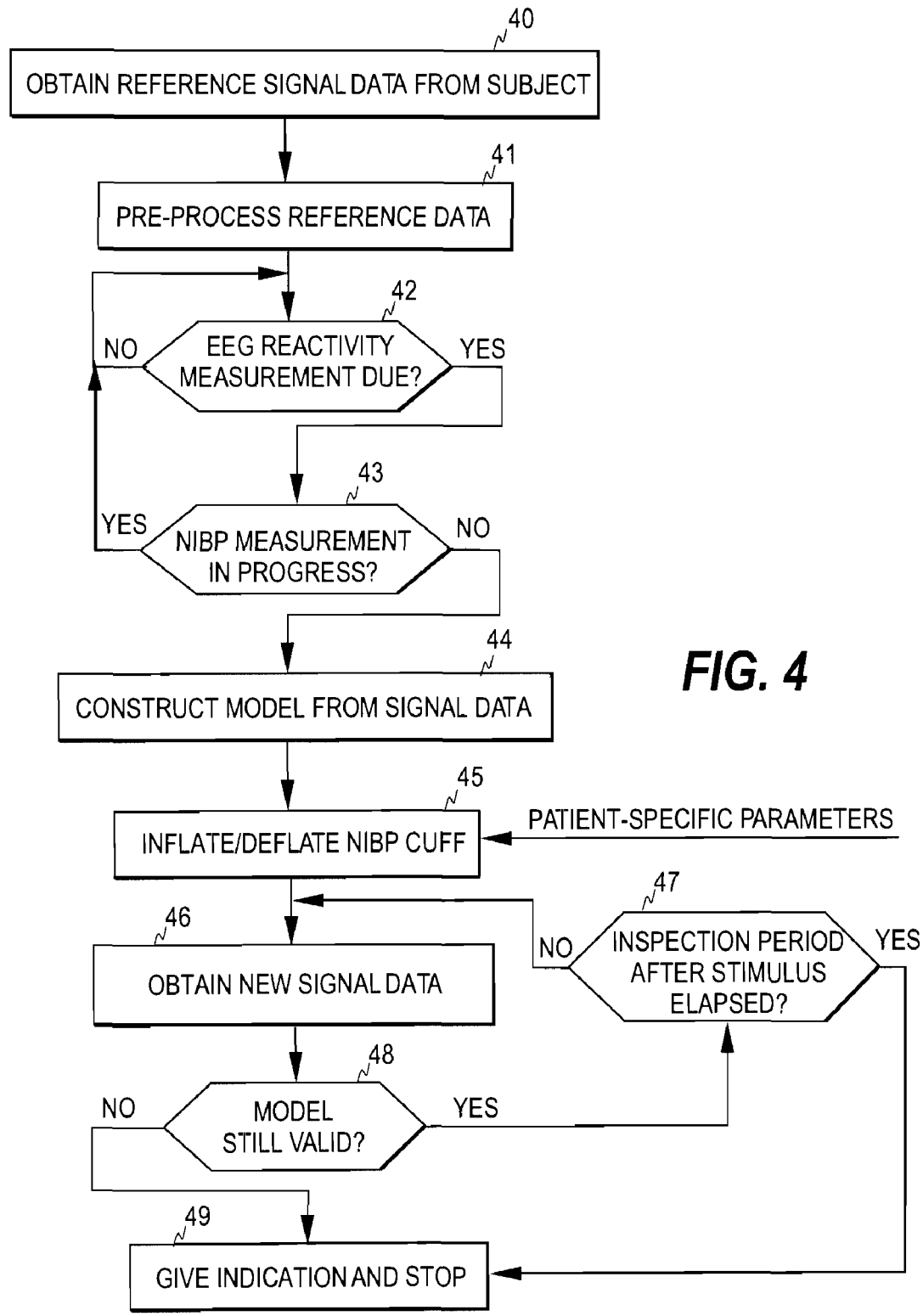
FIG. 4 is a flow diagram illustrating another embodiment for the reactivity determination in the embodiment of FIG. 1.

FIG. 4 illustrates another embodiment of the operation of the EEG reactivity module of FIG. 1. Steps 40-42 correspond, respectively, to steps 31-33 of FIG. 3, i.e. in these steps a time series of EEG signal data is acquired and filtered to exclude high- and low-frequency artifacts, and the need for the EEG reactivity measurement is monitored. When the need is detected at step 42, the EEG reactivity module again checks whether the NIBP cuff is available for the reactivity measurement (step 43).

This embodiment is based on a signal model constructed for the EEG signal from the EEG signal data obtained from the patient. The signal data obtained initially from the patient may therefore be termed reference signal data, since it is employed at step 44 to construct a valid signal model for the current EEG time series. The signal model constructed enables prediction of signal values for the time series and a valid signal model meets predetermined criteria in the prediction. For example, the signal model may be regarded as a valid model as long as the prediction error remains below a certain threshold value.

A stimulus may then be given by successively inflating and deflating the NIBP cuff according to patient-specific parameters (step 45). EEG signal data subsequent to the stimulus is then obtained from the time series at step 46 and the obtained data is utilized to test whether the signal model remains as a valid model for the signal also after the stimulus, step 48. If the test indicates that the model is not any more valid, it is decided that reactivity is present and the user is informed of the presence of reactivity (step 49). Various decision rules may be employed to decide when the model turns into an invalid model. For example, the model may have to be an invalid model continuously for a certain period, before it is regarded as an invalid model.

If the constructed signal model remains as a valid signal model for a certain inspection period, such as 30 seconds, after the stimulus, the process decides that no reactivity is present and quits the testing. The user is informed that no reactivity was found (steps 46 to 49).

FIG. 4 illustrates the method for one stimulus signal (inflation/deflation). If a new stimulus is given, the above steps may be repeated, i.e. the signal model is constructed before each stimulus to ensure that the model corresponds to the current EEG of the patient. Furthermore, if the stimulus signal is not supplied immediately after the signal model is available, the validity of the model may be tested already prior to the stimulus to ascertain that the model remains as a valid model until the time instant of the stimulus.

Automatic EEG reactivity measurement based on a signal model is disclosed in Applicant's U.S. patent application Ser. No. 11/674,732. Since the present invention does not relate to the actual reactivity determination, the determination process is not discussed in more detail in this context. Reference is made to the above-mentioned U.S. patent applications of the Applicant, which discuss these processes in more detail.

FIG. 5 illustrates one embodiment of the system or apparatus according to the invention. It is assumed here that the apparatus is according to the embodiment of FIG. 2 in which electrical stimuli are supplied to the patient through the same electrodes from where the EEG signal is acquired. In this embodiment, three EEG electrodes $11_1$ to $11_3$ are attached to the forehead of the patient 100. Electrodes $11_1$ and $11_3$ are active electrodes, while the middle electrode $11_2$ is a ground electrode.

For supplying the stimulus signal, the apparatus includes a signal generator 53 connected to electrodes $11_1$ and $11_3$ through switches 51 and 52 and corresponding wires A and B. The current supplied through the electrodes is high enough to cause a sensation, but may also be higher to cause muscle contraction, or even sensation of pain. The current supplied is typically of the order of a few tens of milliamperes.

The EEG signal data obtained from the electrodes is supplied to an amplifier stage 54, in which the signal is amplified before being sampled and converted into digitized format in an A/D converter 55. The digitized signal data is supplied to a control unit 56 which may comprise one or more computer units or processors.

The control unit is provided with a memory or database 57 holding the digitized signal data obtained from the electrodes. The memory or database may also store the EEG reactivity algorithm and the parameters defining the stimulation pattern, which may be patient-specific. The control unit executes the stored algorithm, whereby a measure of the EEG reactivity is obtained. During the execution, the control unit controls the signal generator and switches 51, 52 in order to supply a stimulus through electrodes $11_1$ and $11_3$ to the patient. Furthermore, the control unit may label the EEG signal data obtained during the stimulation so that the actual EEG measurement process is able to identify the EEG segments obtained during the stimulation and is able to inform the user of the device of the said segments in the EEG waveform.

The reactivity indicator, its trend, and user notifications may be displayed on the screen of a monitor 58, which forms part of the user interface of the device. Although a control unit comprising one computer unit or one processor may perform the above steps, the processing of the data may also be distributed among different units/processors (servers) within a network, such as a hospital LAN (local area network). The apparatus of the invention may thus also be implemented as a distributed system. Moreover, it is also possible to carry out the reactivity determination off-line based on the labeled signal data stored in advance in the memory.

The user may control the operation of the monitoring device through a user input device 59, such as a keyboard. The control unit 56 may control the signal generator according to the commands given by the user from the user input device or according to a predetermined stimulation schedule stored in the memory of the apparatus.

Figure 6:
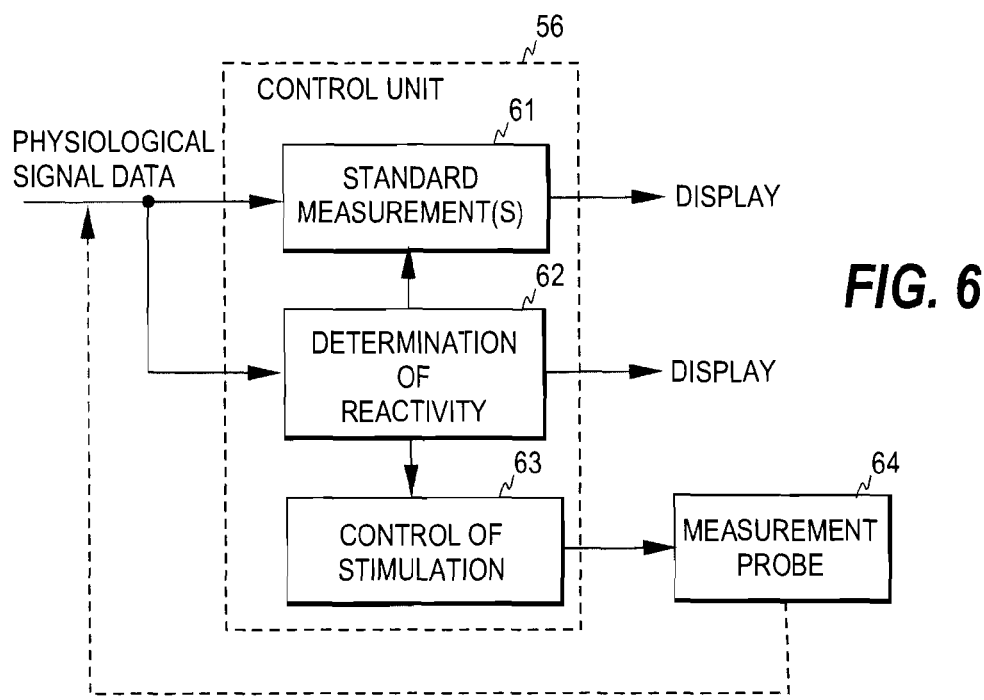

FIG. 6 illustrates the operational entities of the control unit. First, the control unit includes one or more measurement modules 61 for performing the standard physiological measurements of a patient monitoring device, such as an EEG measurement, an ECG measurement, and/or a NIBP measurement. The EEG or ECG signal obtained from the patient is also supplied to the reactivity module comprising a first module 62 for determining the reactivity and a second module 63 for supplying the stimuli to the measurement probe 64 in question. As discussed above, the determination includes applying a time reference corresponding to a stimulus and aligning the physiological signal data temporally with the time reference.

Since conventional patient monitors are provided with audio alarms, the control unit may also generate an audio signal when commanding the stimulation module to supply a stimulus signal. The content of the audio signal may be patient-specific.

For automatic and continuous assessment of the reactivity, the first module may comprise a test algorithm for finding out an appropriate stimulation strength for the patient. In the test algorithm, the strength of the stimulus may be increased in small steps to find out the level at which reactivity is first detected. For the automatic and continuous assessment of reactivity, the long-term strength of the stimulus is then set according to the found reactivity threshold. The patient-specific reactivity threshold allows sensitive tracking of changes in patient's status.

Above, the invention was employed for assessing the EEG reactivity of a patient. However, depending on whether a test of the reactivity of another physiological signal than the EEG provides valuable information about the patient, the same mechanism may be used in connection with said another physiological signal. Therefore, the invention is not necessarily limited to the context of EEG.

A conventional patient monitor may also be upgraded to enable the monitor to determine the physiological signal reactivity of a patient.

Such an upgrade may be implemented by delivering to the monitoring device a plug-in software module that enables the device to supply the stimuli through a first measurement probe of the device and to calculate the reactivity based on the time series of the physiological signal data received through a second measurement probe of the device, which may or may not be the same as the first measurement probe. The software module may be delivered, for example, on a data carrier, such as a CD or a memory card, or through a telecommunications network. As discussed above, the plug-in module is especially suitable for a monitoring device provided with automatic blood pressure evaluation.

Although the invention was described above with reference to the examples shown in the appended drawings, it is obvious that the invention is not limited to these, but may be modified by those skilled in the art without departing from the scope of the invention. For example, in a simple embodiment, the actual measurement displays the EEG and/or ECG waveform and labels the moments/periods of stimulation so that a clinician may evaluate the EEG/ECG waveform and the reactivity by visually examining the waveform.

We claim:

1. A method for assessing physiological signal reactivity of a subject, the method comprising:
   receiving physiological signal data from a subject through at least a first measurement probe and a second measurement probe attached to the subject, wherein the first measurement probe includes a plurality of electrodes that all receive the physiological signal data from the subject;
   supplying a stimulus to the subject through at least one electrode of the first measurement probe, wherein the at least one electrode of the first measurement probe also receives physiological signal data from the subject; and
   determining whether reactivity caused by the stimulus is present in physiological signal data received through the second measurement probe.

2. A method according to claim 1, wherein the determining includes determining whether reactivity caused by the stimulus is present in the physiological signal data received through the second measurement probe, in which the second measurement probe comprises a set of EEG electrodes for receiving EEG signal data from the subject.

3. A method according to claim 2, wherein the supplying includes supplying the stimulus through the first measurement probe, in which the stimulus is an electrical stimulus and the plurality of electrodes of the first measurement probe comprises a set of ECG electrodes.

4. A method according to claim 1, wherein the supplying includes supplying the stimulus through the first measurement probe, in which the stimulus is an electrical stimulus and the plurality of electrodes of the first measurement probe comprises a set of EEG electrodes.

5. A method according to claim 1, wherein the supplying includes supplying the stimulus through the first measurement probe, in which the stimulus is an electrical stimulus and the plurality of electrodes of the first measurement probe comprises a set of ECG electrodes.

6. A method according to claim 1, further comprising
   repeating the supplying and determining; and
   defining whether changes occur over time in the reactivity of the subject.

7. A method according to claim 6, further comprising optimizing the strength of the stimulus for the subject.

8. A method for assessing physiological signal reactivity of a subject, the method comprising:
   receiving physiological signal data from a subject through a first measurement probe and a second measurement probe attached to the subject;
   supplying a stimulus to the subject through the first measurement probe, wherein the supplying includes pressurizing a blood pressure probe, the first measurement probe comprising the blood pressure probe, wherein the first measurement probe also receives physiological signal data from the subject; and
   determining whether reactivity caused by the stimulus is present in physiological signal data received through the second measurement probe.

9. A method according to claim 8, wherein the pressurizing is carried out in connection with the subject's blood pressure measurement.

10. A method according to claim 8, wherein the second measurement probe comprises a set of EEG electrodes.

11. An apparatus for assessing physiological signal reactivity of a subject, the apparatus comprising:
    a measurement module configured to receive physiological signal data from a subject;
    a first measurement probe attachable to the subject, the first measurement probe including a plurality of electrodes, wherein all of the plurality of electrodes are configured to receive the physiological signal data from the subject;
    a second measurement probe attachable to the subject and configured to receive the physiological signal data from the subject;
    a stimulation module configured to stimulate the subject through at least one electrode of the first measurement probe; and
    a reactivity determination module configured to determine whether reactivity caused by the stimulus is present in physiological signal data received through the second measurement probe.

12. An apparatus according to claim 11, wherein the plurality of electrodes of the first measurement probe comprises a set of EEG electrodes and the stimulation module is configured to supply an electrical signal to at least one electrode of the set to stimulate the subject.

13. An apparatus according to claim 12, wherein the second measurement probe comprises said set of EEG electrodes.

14. An apparatus according to claim 11, wherein the plurality of electrodes of the first measurement probe comprises a set of ECG electrodes and the stimulation module is configured to supply an electrical signal to at least one electrode of the set to stimulate the subject.

15. An apparatus according to claim 11, wherein the reactivity module is further configured to control the strength of a stimulus signal supplied by the stimulation module.

16. An apparatus according to claim 15, wherein the reactivity module is further configured to find out a strength value above which reactivity is present.

17. An apparatus for assessing physiological signal reactivity of a subject, the apparatus comprising:
- a measurement module configured to receive physiological signal data from a subject;
- a first measurement probe attachable to the subject, the first measurement probe being configured to receive the physiological signal data from the subject, wherein the first measurement probe comprises a pressurizable cuff for measuring blood pressure;
- a second measurement probe attachable to the subject and configured to receive the physiological signal data from the subject;
- a stimulation module configured to stimulate the subject through the first measurement probe, wherein the stimulation module is configured to pressurize the cuff to stimulate the subject; and
- a reactivity determination module configured to determine whether reactivity caused by the stimulus is present in physiological signal data received through the second measurement probe.

18. An apparatus according to claim 17, wherein the second measurement probe comprises a set of EEG electrodes.

19. A method of assessing physiological signal reactivity of a subject, the method comprising the steps of:
- receiving physiological signal data from a subject through a first measurement probe including a plurality of electrodes attached to the subject, wherein all of the plurality of electrodes are utilized in receiving the physiological signal data;
- supplying a stimulus to the subject through at least one electrode of the first measurement probe such that the at least one electrode both supplies the stimulus to the patient and receives physiological signal data from the patient; and
- determining whether reactivity caused by the stimulus is present in the physiological signal data received through the first measurement probe.

20. The method according to claim 19 wherein the plurality of electrodes of the first measurement probe comprises a set of EEG electrodes for receiving EEG signal data from the subject.

* * * * *